United States Patent
Hynes et al.

(10) Patent No.: US 9,872,711 B2
(45) Date of Patent: Jan. 23, 2018

(54) SPINAL IMPLANT SYSTEM AND METHOD

(71) Applicant: Warsaw Orthopedic, Inc., Warsaw, IN (US)

(72) Inventors: Richard A. Hynes, Melbourne Beach, FL (US); Alan Rezach, Atoka, TN (US); Rodney R Ballard, Lakeland, TN (US)

(73) Assignee: Warsaw Orthopedic. Inc., Warsaw, IN (US)

( * ) Notice: Subject to any disclaimer, the term of this patent is extended or adjusted under 35 U.S.C. 154(b) by 11 days.

(21) Appl. No.: 14/520,054

(22) Filed: Oct. 21, 2014

(65) Prior Publication Data
US 2016/0106477 A1    Apr. 21, 2016

(51) Int. Cl.
*A61B 17/70*     (2006.01)
*A61B 17/56*     (2006.01)

(52) U.S. Cl.
CPC ...... *A61B 17/7044* (2013.01); *A61B 17/7032* (2013.01); *A61B 17/7037* (2013.01); *A61B 17/7055* (2013.01); *A61B 17/7059* (2013.01); *A61B 2017/564* (2013.01)

(58) Field of Classification Search
CPC ............ A61B 17/7044; A61B 17/7001; A61B 17/7035; A61B 17/7055; A61B 17/7059
See application file for complete search history.

(56) References Cited

U.S. PATENT DOCUMENTS

| | | | | |
|---|---|---|---|---|
| 5,735,852 | A * | 4/1998 | Amrein ............. | A61B 17/7044 606/278 |
| 2008/0300634 | A1* | 12/2008 | Gray .................. | A61B 17/7059 606/280 |
| 2010/0268279 | A1* | 10/2010 | Gabelberger ...... | A61B 17/7035 606/278 |
| 2011/0224737 | A1* | 9/2011 | Lewis ................ | A61B 17/1728 606/290 |
| 2012/0022595 | A1* | 1/2012 | Pham ................. | A61B 17/7032 606/278 |
| 2013/0085534 | A1* | 4/2013 | Hainard ............. | A61B 17/7055 606/278 |
| 2015/0025576 | A1* | 1/2015 | Taylor ................ | A61B 17/7035 606/250 |
| 2015/0272637 | A1* | 10/2015 | Buttermann ........... | A61B 17/80 606/70 |

* cited by examiner

*Primary Examiner* — Ellen C Hammond

(57) ABSTRACT

A spinal implant for use with a surgical treatment comprises a plate including a surface that defines a first cavity and a second cavity. The first cavity is oriented to implant a multi-axial fastener with a sacrum. The second cavity is oriented to implant a fastener with an ala of a sacrum. Systems and methods of use are disclosed.

18 Claims, 17 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Fasteners may also be attached to iliac bone. This disclosure describes an improvement over these prior art technologies.

SUMMARY

In one embodiment, a spinal implant for use with a surgical treatment is provided. The spinal implant comprises a plate including a surface that defines a first cavity and a second cavity. The first cavity is oriented to implant a multi-axial fastener with a sacrum. The second cavity is oriented to implant a fastener with an ala of a sacrum. Systems and methods of use are disclosed.

BRIEF DESCRIPTION OF THE DRAWINGS

The present disclosure will become more readily apparent from the specific description accompanied by the following drawings, in which:

FIG. 3b is a side view of the component of the system shown in FIG. 3a;

DETAILED DESCRIPTION

Figure 1:
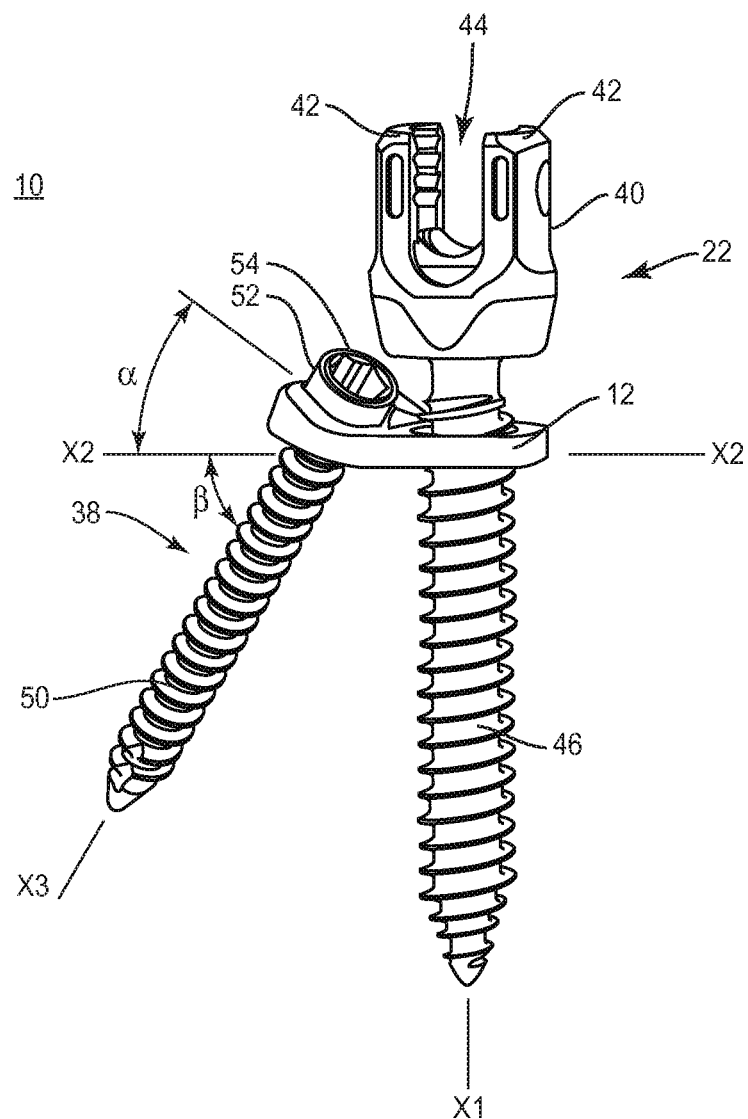
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the systems and methods of the present disclosure are employed with a spinal joint and fusion, for example, with a cervical, thoracic, lumbar and/or sacral region of a spine. In one embodiment, the systems and methods can be employed with a spinal fusion, such as, for example, a midline posterior joint fusion.

In one embodiment, the system includes an implant, such as, for example, a plate configured for engagement with two screws. In some embodiments, the system includes a dual screw sacral plate configured for use with a midline pedicle screw approach. In one embodiment, the system includes a screw that is configured for alignment with a sacral trajectory and/or surgical pathway and a screw that is configured for alignment with a sacral alar trajectory and/or surgical pathway. In one embodiment, the system includes a plate that is configured for positioning on a left side or a right side of a patient's body. In one embodiment, the system includes a kit comprising one or more alar screws that are provided with various lengths, such as, for example, 30 millimeters (mm), 35 mm, 40 mm, 45 mm and/or 50 mm. In one embodiment, the system includes a surgical instrument, such as, for example, an awl that is connected with a plate for insertion adjacent a surgical site along an S1 trajectory and/or surgical pathway. In one embodiment, the system includes an awl utilized to guide an alar screw along an alar trajectory and/or surgical pathway. In some embodiments, the same awls can be utilized for left oriented plates or right oriented plates.

In one embodiment, the system includes a plate configured to be attachable to vertebrae in a cephalad-caudal orientation. In one embodiment, the system includes a plate including two cavities. In one embodiment, one of the cavities includes an angular orientation relative a surface of a plate. In one embodiment, the angular orientation is 20 degrees in a lateral direction and/or 45 degrees in a cephalad-caudal direction.

In one embodiment, the system includes a plate configured to be attachable to vertebrae in a medial-lateral orientation. In one embodiment, the system includes a plate positioned above an S1 foramen during a surgical procedure. In one embodiment, the plate is configured for disposal of a multi-axial bone screw (MAS) and a sacral alar bone screw. In one embodiment, the MAS includes a receiver that can be oriented to prevent the bone screw from backing out of an S1 vertebra. In some embodiments, the angles of the bone screws may be selectively adjusted. In some embodiments, an interface between a plate and the MAS facilitates a tight fit to prevent the MAS from backing out of the plate and/or tissue. In one embodiment, the MAS interlocks into a plate such that resistance from being pulled out and/or backing out is increased.

In one embodiment, the system includes a plate configured for attachment to a sacrum and is symmetrically configured such that it may be disposed on either side of the sacrum of the patient's body. In one embodiment, the plate is asymmetric and comprises a left version and a right version. In one embodiment, a bone fastener comprises a headless bone screw having a diameter of 6.5 mm, 7.5 mm or 8.5 mm. In one embodiment, the bone fastener comprises a 4 mm dual lead thread. In one embodiment, the bone fastener is attached to an S1 vertebra at an angular orientation of 25 degrees in a medial direction and/or 25 degrees in a lateral direction.

In one embodiment, the system includes inserts configured to be positioned in a first cavity and/or a second cavity of a plate. In one embodiment, an insert includes an outer thread configured to facilitate engagement with a cavity. In one embodiment, the insert includes an inner thread configured to facilitate engagement with a bone screw.

In one embodiment, the present system is employed with a method for implanting components of the system with one or more vertebra of a patient. In one embodiment, the system includes an insert configured to receive a bone fastener and the method includes the step of inserting the bone fastener into a plate. In one embodiment, the method includes the step of inserting an awl through a first cavity of a plate and into an S1 vertebra to stabilize the plate and establish a desired trajectory. In one embodiment, the awl locks into the plate to resist being pulled out and/or backing out axially.

In one embodiment, the method includes the step of positioning a plate about an S1 awl and a bone fastener is inserted through the plate. In one embodiment, the method includes the step of snapping a plate onto an awl guide holder. In one embodiment, the method includes the step of attaching the awl guide holder with the plate and placing the components in a desired position on a sacrum and the awl is malleted in place. In one embodiment, the method includes the step of placing a sacral nail screw through the awl guide holder and/or loaded in the awl guide holder and is malleted in place, except for the remaining 3-5 mm of a pilot hole. In one embodiment, the method includes the step of screwing a fastener in the final 3-5 mm of the pilot hole and screwed in with threads on a nose and a neck of the nail screw.

In one embodiment, the method includes the step of removing the awl guide holder and leaving the nail screw in a selected position. In one embodiment, the method includes the step of providing a bone fastener with a preloaded nub, which is screwed into a plate and locking the nub into the plate and resisting potential back out of the nail screw from a cavity and into an ala of a sacrum. In one embodiment, the method includes pulling out an awl from a first cavity of a plate and driving a MAS into a pilot hole established by the awl.

In one embodiment, a bone fastener comprises a nail having a spherical head and a bone fastener comprising a MAS. In one embodiment, the system comprises a plate cover or a layer configured to lock a spherical head of a nail in position. In one embodiment, a bone fastener is received in a first cavity of the plate to engage an S1 vertebra. In one embodiment, a bone fastener is received in a second cavity of a plate to engage an ala of a sacrum.

In one embodiment, the system is employed with a method for implanting components of the system with vertebrae of a patient. In one embodiment, the method includes the step of threading an awl through a first cavity of a plate and into an S1 vertebra to stabilize the plate and establish a desired trajectory. In one embodiment, the method includes the step of driving an alar nail through a cavity of a plate and into an ala of a sacrum. In one embodiment, the method includes the step of drawing out an awl from a cavity of a plate. In one embodiment, the method includes the step of positioning a plate cover over the plate to lock an alar nail in a selected position. In one embodiment, the method includes the step of threading an insert into a cavity of a plate and passing a MAS through a cavity of the plate and driving the MAS into a pilot hole established by an awl. In some embodiments, the insert may be sized to accommodate use of a variety of MAS sizes. In one embodiment, the inserts may be color coded. In one embodiment, the insert is configured to apply downward pressure on the plate cover to lock the spherical head of the alar nail in place.

In one embodiment, the system includes a plate for engagement with a sacrum having a low profile. In one embodiment, the system is employed with a method that includes the step of threading an awl through a cavity of a plate and into an S1 vertebra to stabilize the plate and establish a desired trajectory. In one embodiment, the method includes the step of driving an alar nail through a cavity of a plate and into an ala of a sacrum. In one embodiment, the alar nail comprises proximal threads to engage threads on an inner surface of a cavity of the plate. In one embodiment, the method includes the step of removing the awl from a cavity of a plate. In one embodiment, the method includes the step of threading an insert into a cavity of a plate and passing a MAS through the cavity and driving the MAS into a pilot hole established by the awl.

In some embodiments, the present system and/or method is used with surgical navigation, such as, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In one embodiment, one or all of the components of the surgical system are disposable, peel-pack or pre-packed sterile devices. One or all of the components of the surgical system may be reusable. The surgical system may be configured as a kit with multiple sized and configured components.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3b, there are illustrated components of a spinal implant system 10, in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TOP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

System 10 includes an implant, such as, for example, a plate 12. In one embodiment, plate 12 is configured for disposal in a medial-lateral orientation between a sacrum and a sacral ala. Plate 12 includes a substantially rectangular configuration and defines a longitudinal axis X1. In some embodiments, plate 12 can be variously configured, such as, for example, oval, oblong, triangular, square, polygonal, irregular, uniform, non-uniform, variable, hollow and/or tapered. Plate 12 includes a wall 14 that defines an axis X2 and defines a wall thickness t1. Wall 14 includes an inner surface 16 and an outer surface 18. In one embodiment, axis X2 is disposed in a perpendicular orientation relative to axis X1. In some embodiments, axis X2 may be disposed at various orientations relative to axis X1, such as, for example, transverse, and/or angular orientations, such as acute or obtuse.

Surface 16 defines a cavity, such as, for example, an opening 20. Opening 20 is configured to receive a fastener, such as, for example, a MAS 22. Opening 20 is aligned with axis X1. In some embodiments, opening 20 is aligned with a surgical pathway, approach and/or trajectory, as described herein, to orient MAS 22 for implantation with tissue, such as, for example, an S1 vertebra of a sacrum S, as shown for example in FIGS. 11-14. In some embodiments, opening 20 is aligned with a surgical pathway, approach and/or trajectory that communicates with a posterior mid-line surgical pathway, approach and/or trajectory, as described herein.

Opening 20 includes an engagement surface 24 configured to facilitate engagement with screw 22. In one embodiment, surface 24 is smooth. In one embodiment, surface 24 includes a threaded surface configured to facilitate engagement with a threaded shaft of MAS 22, as described herein.

Figure 2A:
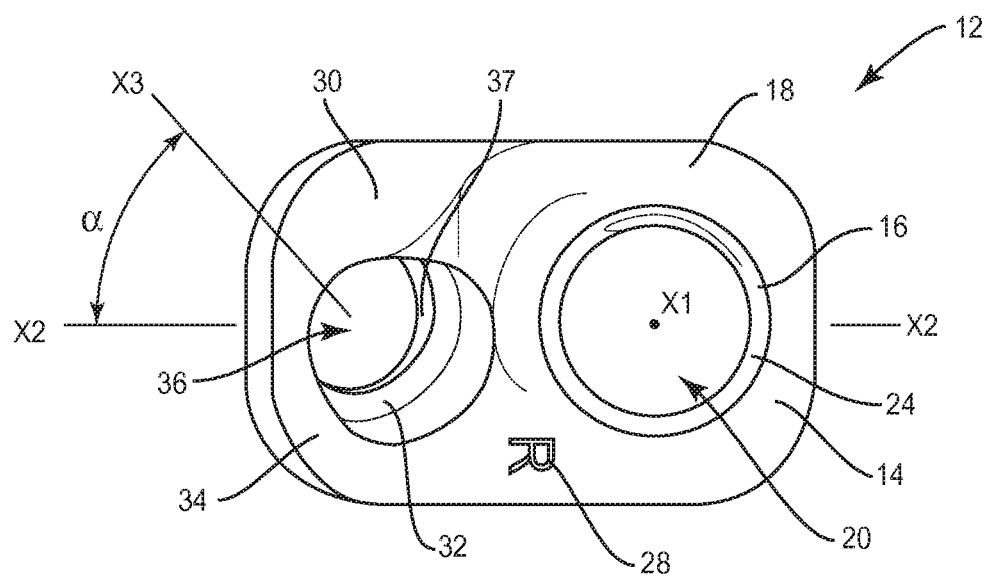
FIG. 2a is a top view of a component of the system shown in FIG. 1.
Figure 2B:
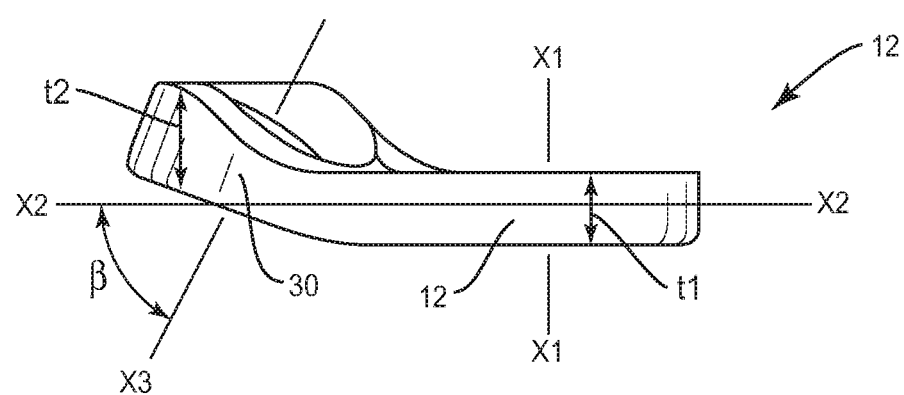
FIG. 2b is a side view of the component of the system shown in FIG. 1.
Figure 3A:
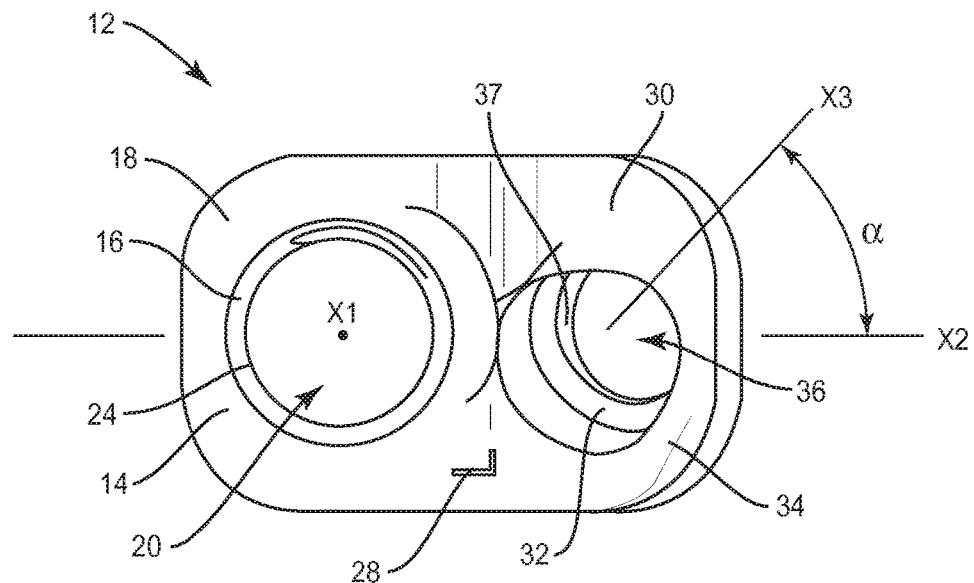
FIG. 3a is a top view of a component of one embodiment of a system in accordance with the principles of the present disclosure.
Figure 3B:
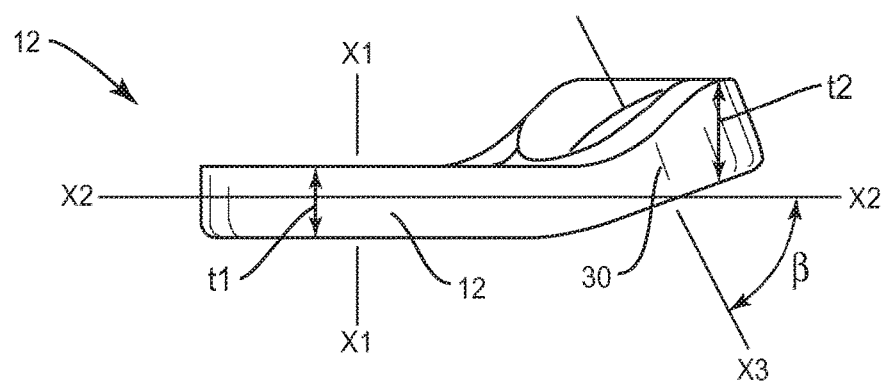

Surface 18 is configured for engagement with tissue of the S1 vertebra. In some embodiments, surface 18 may include alternate surface configurations, such as, for example, rough, arcuate, undulating, mesh, porous, semi-porous, dimpled and/or textured to facilitate engagement with tissue. In one embodiment, plate 12 includes visual indicia configured to provide configuration and/or a dimension of plate 12. In some embodiments, system 10 may comprise a kit including a plurality of plates with visual indicia indicative of their respective configuration and dimension. In some embodiments, the visual indicia may include color coding to provide configuration and/or a dimension of plate 12. In some embodiments, plate 12 has indicia 28 that displays configuration information for disposal of plate 12 on a right side of a patient, as shown in FIGS. 2a and 2b, or a left side of a patient, as shown in FIGS. 3a and 3b.

Plate 12 includes a wall 30 that defines a wall thickness t2. In one embodiment, thickness t1 is less than thickness t2. In one embodiment, thickness t1 is greater than thickness t2. In one embodiment, thickness t1 is equal to thickness t2. Wall 30 includes an inner surface 32 and an outer surface 34.

Surface 32 defines a cavity, such as, for example, an opening 36. Opening 36 defines an axis X3 and is configured to receive a fastener, such as, for example, a sacral alar screw 38. Opening 36 is configured for disposal of alar screw 38 and aligns alar screw 38 with axis X3. As such, the longitudinal axis of alar screw 38 is co-axial with axis X3. In some embodiments, axis X3 is disposed at a compound angle relative to axis X1 and/or axis X2. In some embodiments, axis X3 is disposed at a compound angle relative to axis X2, which includes orientation of axis X3 at an angle α, for example in a lateral direction, relative to axis X2 and at an angle β, for example in a cephalad-caudal direction, relative to axis X2, as shown in FIGS. 1-3b. As such, for example, MAS 22 is aligned with axis X1 for implantation with an S1 vertebra and alar screw 38 is aligned with axis X3 for implantation with an alar region of a sacrum to attach plate 12 with a sacrum, as described herein. In some embodiments, axis X3 may be oriented at a single angle relative to axis X1 and/or axis X2. In some embodiments, angle α and/or angle β can include an angle in a range of approximately 0 through 90 degrees. In one embodiment, angle α is approximately 20 degrees in a lateral direction and/or angle β is approximately 45 degrees in a cephalad-caudal direction.

In one embodiment, alar screw 38 has varied lengths, such as, for example, 30 mm, 35 mm, 40 mm, 45 mm or 50 mm and/or system 10 can comprise a kit with such variously sized screws 38. In one embodiment, the fastener is a nail. In one embodiment, the fastener is a curved nail.

In some embodiments, opening 36 is oriented to implant alar screw 38 with tissue, such as, for example, an ala of a sacrum. In some embodiments, opening 36 is offset from axis X1. In some embodiments, opening 36 is aligned with a surgical pathway, approach and/or trajectory, as described herein, to orient alar screw 38 for implantation with an alar region of a sacrum. In some embodiments, opening 36 is aligned with a surgical pathway, approach and/or trajectory that communicates with a posterior mid-line surgical pathway, approach and/or trajectory, as described herein.

Opening 36 includes an engagement surface 37 configured to facilitate engagement with alar screw 38. In one embodiment, surface 37 is smooth. In one embodiment, surface 37 includes a threaded surface configured to facilitate engagement with a threaded shaft of alar screw 38, as described herein.

Surface 34 is configured for engagement with tissue of the ala. In some embodiments, surface 34 may include alternate surface configurations, such as, for example, rough, arcuate, undulating, mesh, porous, semi-porous, dimpled and/or textured to facilitate engagement with tissue.

MAS 22 includes a head 40 having a pair of spaced apart arms 42 having an inner surface that defines a U-shaped passageway 44. Passageway 44 is configured for disposal of an implant, such as, for example, a spinal rod (not shown). In some embodiments, all or only a portion of passageway 44 may have alternate cross section configurations, such as, for example, oval, oblong, triangular, square, polygonal, irregular, uniform, non-uniform, offset, staggered, and/or tapered. In some embodiments, arms 42 may be disposed at alternate orientations, relative to the longitudinal axis of MAS 22, such as, for example, transverse, perpendicular and/or other angular orientations such as acute or obtuse, co-axial and/or may be offset or staggered. The inner surface of head 40 includes a thread form configured for engagement with a coupling member, such as, for example, a set screw (not shown). The set screw is threaded with head 40 to attach, fix and/or lock the spinal rod, either provisionally or permanently, with MAS 22 and/or plate 12, as described herein.

MAS 22 includes a shaft 46 configured for penetrating tissue, such as, for example, a sacrum. Shaft 46 has a cylindrical cross-sectional configuration and includes an outer surface having an external thread form. In some embodiments, the external thread form may include a single thread turn or a plurality of discrete threads. In some embodiments, other engaging structures may be located on shaft 46, such as, for example, a nail configuration, barbs, expanding elements, raised elements and/or spikes to facilitate engagement of shaft 46 with tissue.

In some embodiments, all or only a portion of shaft 46 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 46 may include one or a plurality of openings. In some embodiments, all or only a portion of the outer surface of shaft 46 may have alternate surface configurations to enhance fixation with tissue, such as, for example, rough, arcuate, undulating, mesh, porous, semi-porous, dimpled and/or textured. In some embodiments, all or only a portion of shaft 46 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 46 may be cannulated.

In some embodiments, screw 38 is configured for insertion into an ala region of sacrum, as described herein. Screw 38 includes a shaft 50 having a substantially cylindrical cross-section along its length and a head 52. Shaft 50 includes an outer surface having an external thread form. In some embodiments, the external thread form may include a single thread turn or a plurality of discrete threads. Head 52 includes a tool engaging portion 54 configured to engage a surgical tool or instrument, as described herein. In one embodiment, portion 54 includes a hexagonal cross-section to facilitate engagement with a surgical tool or instrument, as described herein. In some embodiments, portion 54 may have alternative cross-sections, such as, for example, rectangular, polygonal, hexalobe, oval, or irregular.

Figure 4:
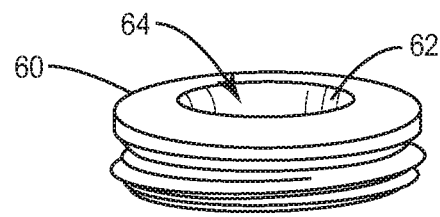
FIG. 4 is a perspective view of a component of one embodiment of a system in accordance with the principles of the present disclosure.
Figure 5:
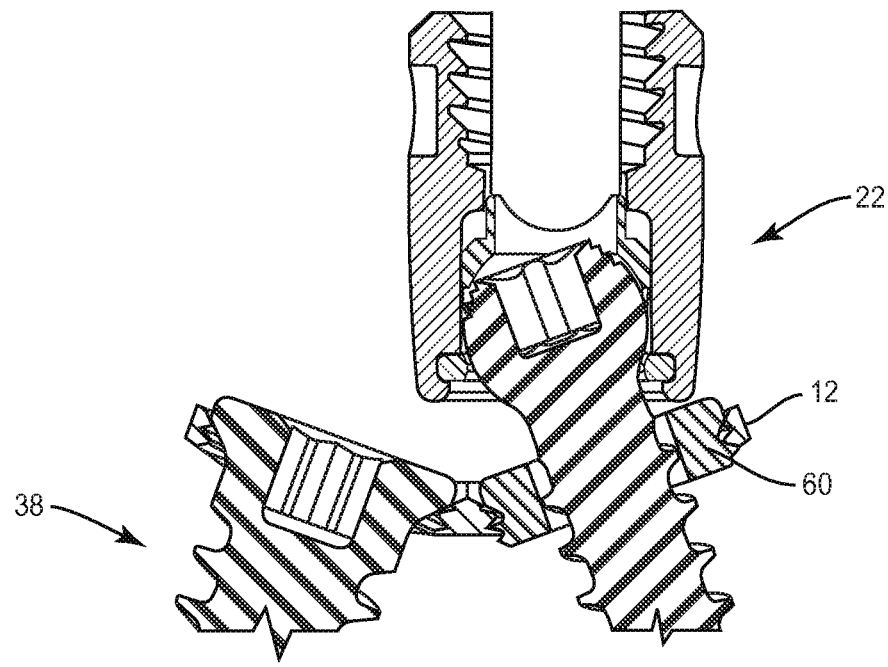
FIG. 5 is a cross section view of components of one embodiment of a system in accordance with the principles of the present disclosure.

In one embodiment, as shown in FIGS. 4 and 5, system 10 includes an insert 60 that is provided for disposal in opening 20 and/or opening 36. Insert 60 includes a surface 62 that defines an opening 64. Insert 60 is configured to facilitate engagement with screw 22 and/or screw 38 and prevent back out of MAS 22 and/or screw 38 from plate 12 and/or tissue. A plurality of inserts 60 can be provided having alternately sized openings 64 to facilitate engagement with various sized screws. In some embodiments, system 10 can comprise a kit including a plurality of inserts 60 that are sized according to the configuration and dimension of a fastener, for example, based on diameters such as 6.5 mm, 7.5 mm or 8.5 mm. In some embodiments, the plurality of inserts 60 may be color coded to identify an insert for employment with a specific configured and/or sized fastener.

Figure 6:
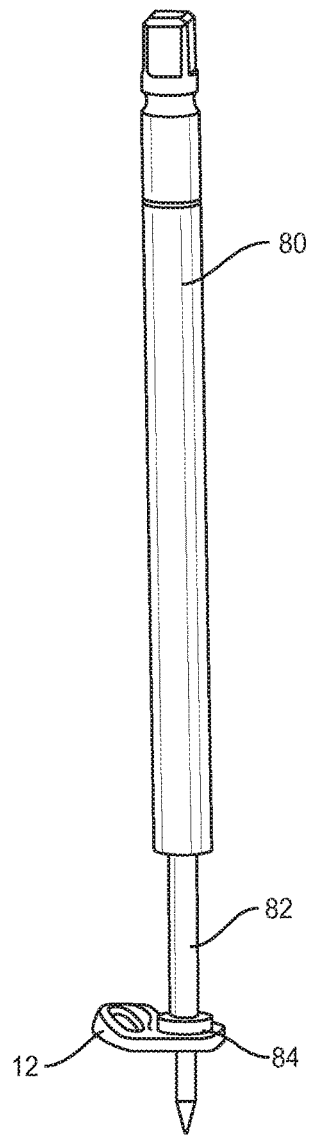
FIG. 6 is a perspective view of components of one embodiment of a system in accordance with the principles of the present disclosure.
Figure 7:
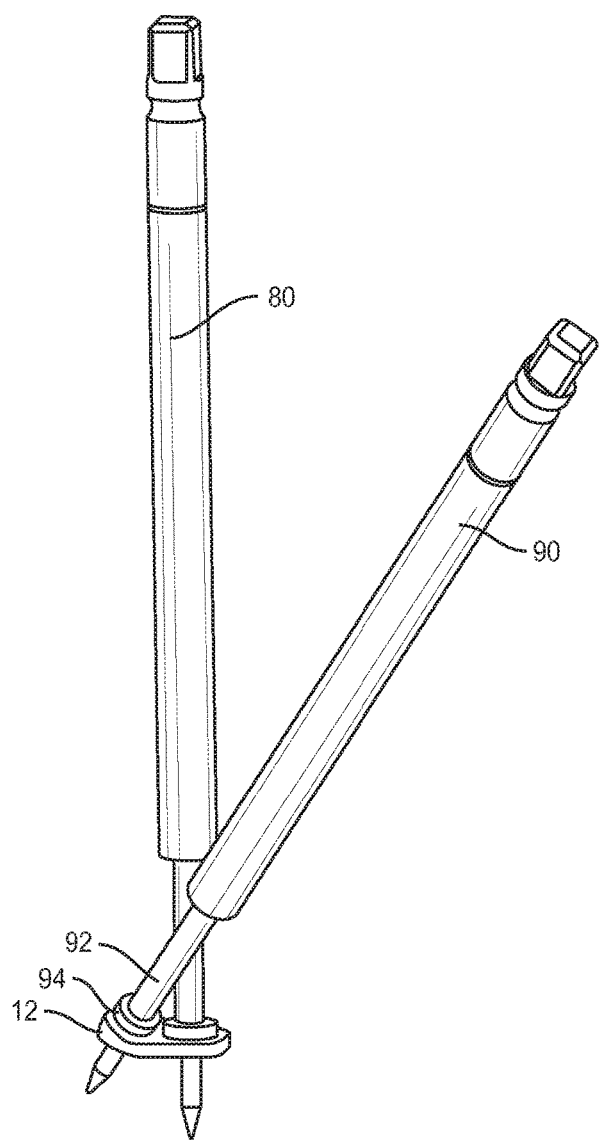
FIG. 7 is a perspective view of components of one embodiment of a system in accordance with the principles of the present disclosure.
Figure 8:
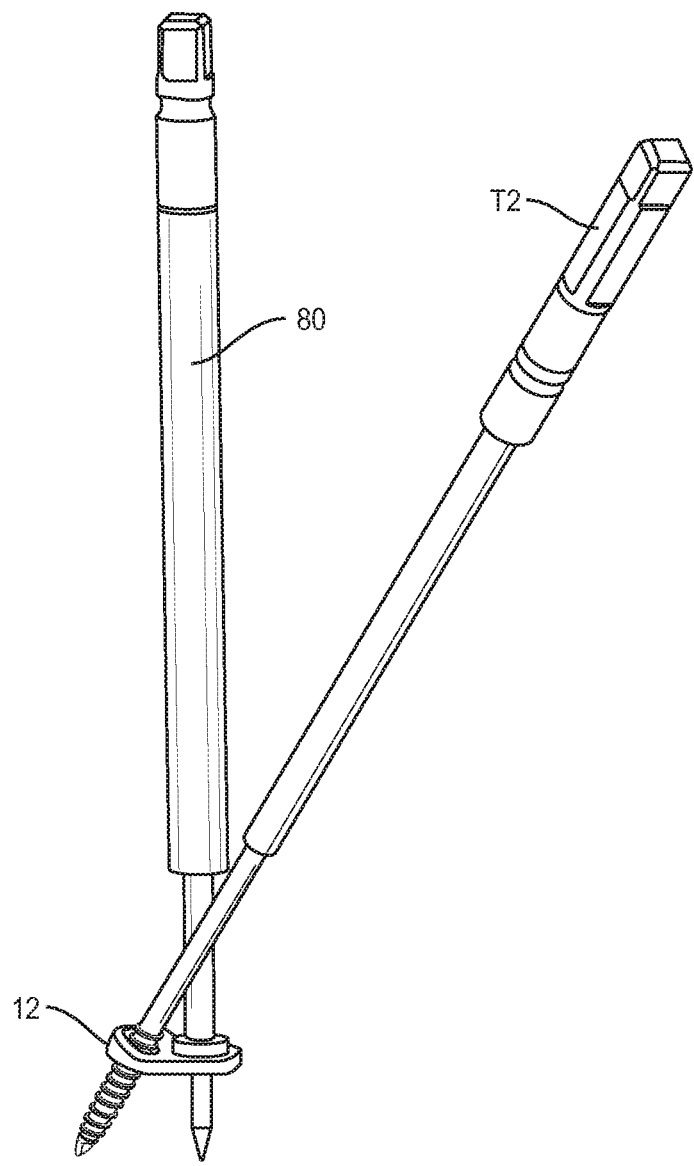
FIG. 8 is a perspective view of components of one embodiment of a system in accordance with the principles of the present disclosure.

In some embodiments, system 10 includes a surgical instrument, such as, for example, an awl 80, as shown in FIGS. 6-8. Awl 80 includes a distal portion 82 having a threaded surface 84 configured for connection with opening 20 of plate 12. Awl 80 is configured for disposal with opening 20 to provisionally fix placement of plate 12 at the surgical site and/or to form a pilot hole in an S1 vertebra of a sacrum for MAS 22. In some embodiments, system 10 includes a surgical instrument, such as, for example, an awl 90. Awl 90 includes a distal portion 92 having a threaded surface 94 configured for connection with opening 36 of plate 12. Awl 90 is configured for disposal with opening 36 to form a pilot hole in an ala region of a sacrum for alar screw 38. In some embodiments, portion 82 and/or portion 92 may be non-threaded.

In assembly, operation and use, system 10, similar to the systems and methods described herein, is employed with a surgical procedure for treatment of a spinal disorder affecting a section of a spine of a patient, as discussed herein. System 10 is employed with a surgical procedure for treatment of a condition or injury of an affected section of the spine including vertebrae V. In one embodiment, as shown in FIGS. 6-14, the components of system 10 are attached to vertebrae V including sacrum S.

In use, to treat a selected section of vertebrae, a medical practitioner obtains access to a surgical site including vertebrae in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway in alignment with a posterior mid-line surgical approach for implantation of components of system 10. A preparation instrument (not shown) can be employed to prepare tissue surfaces of vertebrae, as well as for aspiration and irrigation of a surgical region.

Figure 11:
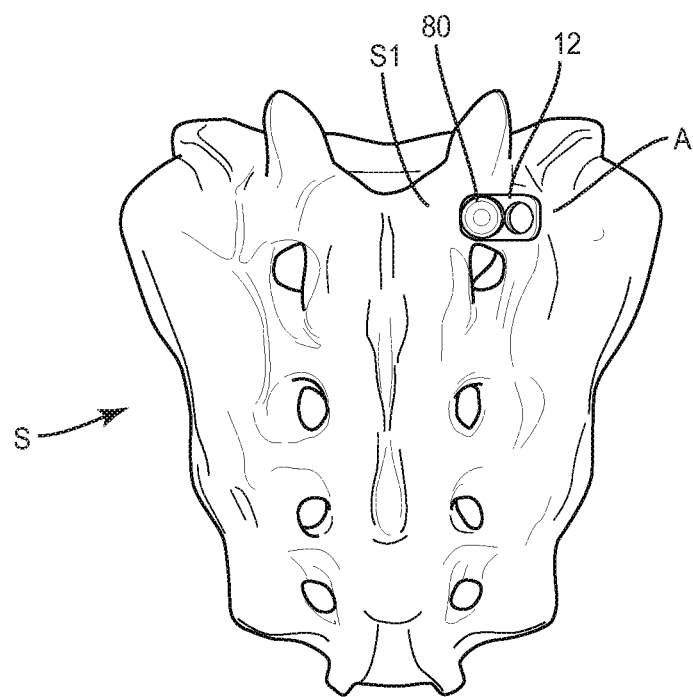
FIG. 11 is a plan view of components of one embodiment of system in accordance with the principles of the present disclosure disposed with vertebrae.

In some embodiments, system 10 comprises a kit including a plurality of plates 12 of varying configuration and/or dimension. In some embodiments, a plate 12 is selected from the kit for employing with the treatment at the surgical site. As shown in FIG. 6, awl 80 is connected with opening 20 of the selected plate 12. Plate 12 is delivered along the surgical pathway to the surgical site, as shown in FIG. 11. Awl 80 is aligned and engaged with sacrum S along a TS1 trajectory, as shown in FIG. 14, to penetrate tissue of sacrum S and facilitate formation of a pilot hole in an S1 vertebra.

Figure 14:
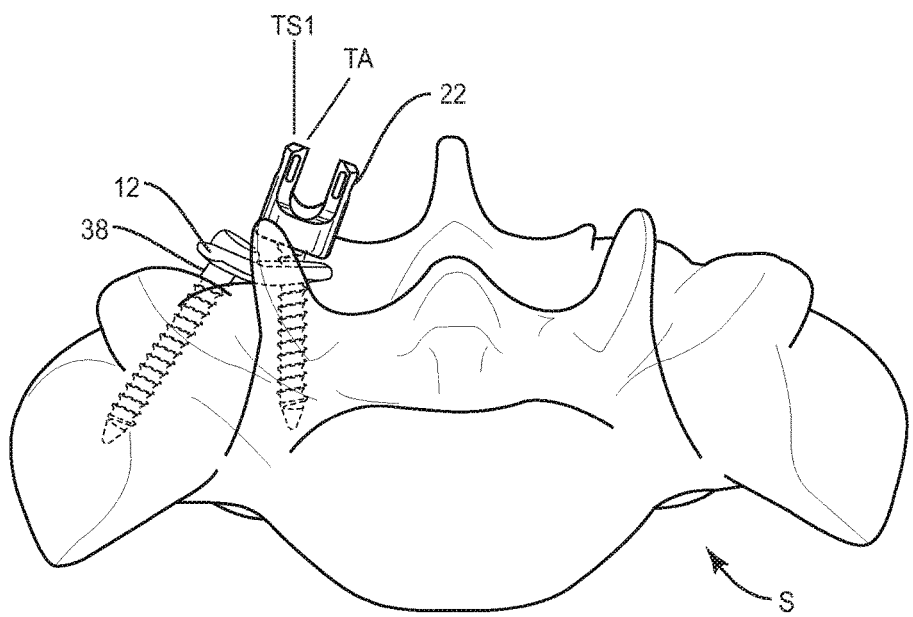
FIG. 14 is an axial view of components of one embodiment of a system in accordance with the principles of the present disclosure disposed with vertebrae.

Awl 90 is aligned and disposed with opening 36, as shown in FIG. 7, along an alar trajectory A1, as shown in FIG. 14, to penetrate tissue of an ala region A of sacrum S and facilitate formation of a pilot hole in region A. A tap T2, as shown in FIG. 8, is utilized to form a pilot hole with the tissue of region A along the alar trajectory TA.

Figure 9:
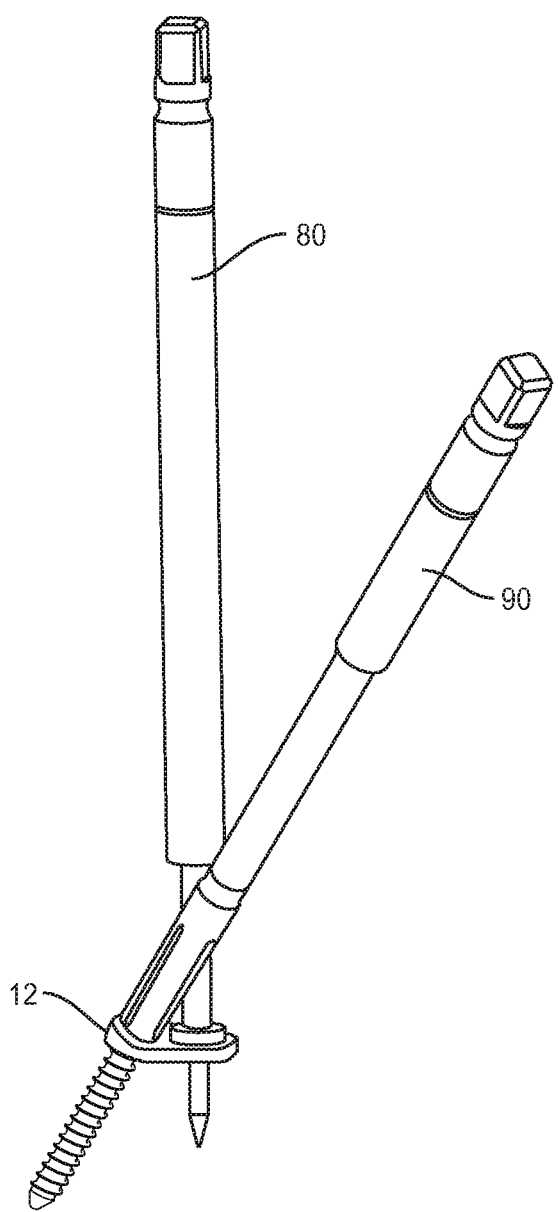
FIG. 9 is a perspective view of components of one embodiment of a system in accordance with the principles of the present disclosure.
Figure 10:
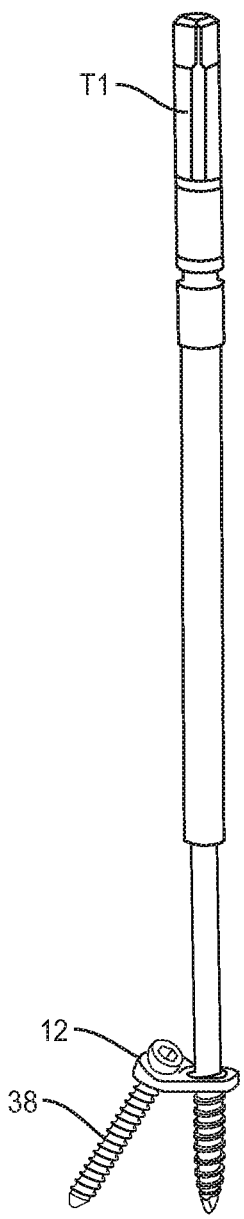
FIG. 10 is a perspective view of components of one embodiment of a system in accordance with the principles of the present disclosure.
Figure 12:
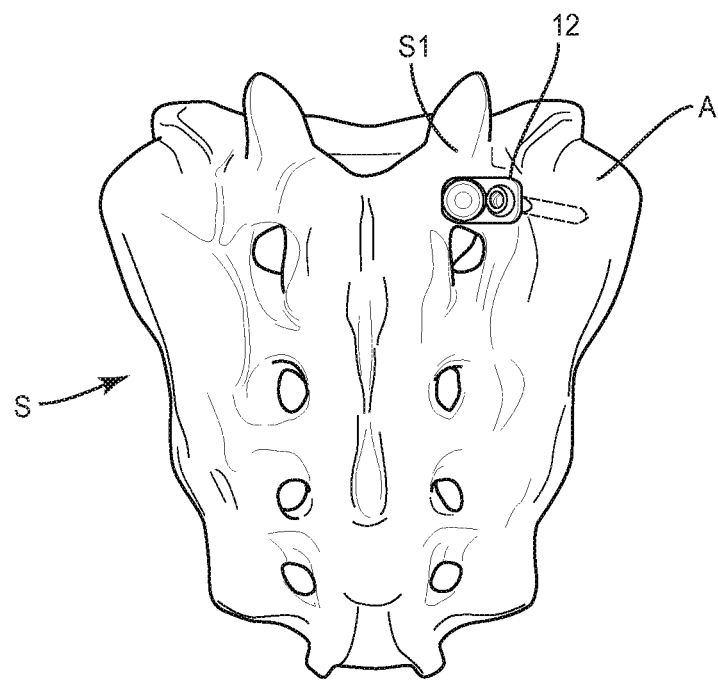
FIG. 12 is a plan view of components of one embodiment of a system in accordance with the principles of the present disclosure disposed with vertebrae.
Figure 13:
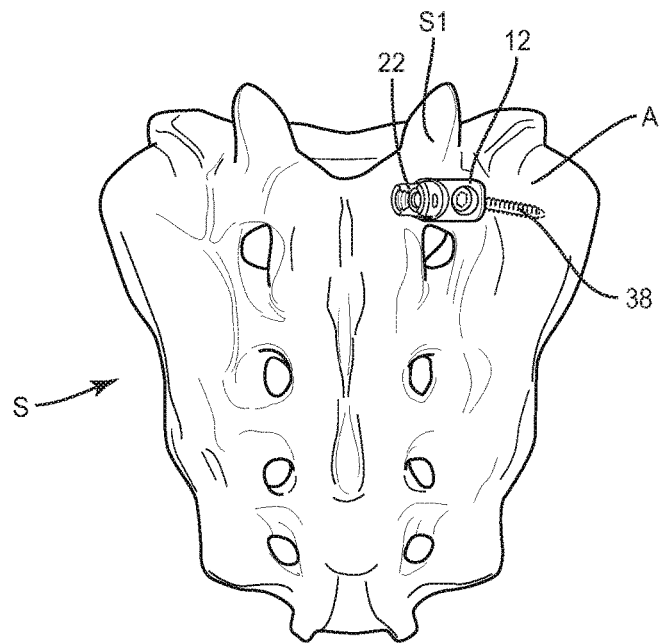
FIG. 13 is a plan view of components of one embodiment of a system in accordance with the principles of the present disclosure disposed with vertebrae.

Awl 90 is removed and alar screw 38 is disposed with opening 36, as shown in FIG. 9, and engaged with region A in threaded fixation, as shown in FIG. 12. A tap T1, as shown in FIG. 10, is utilized to form a pilot hole with the tissue of sacrum S along the S1 trajectory in the S1 vertebra. Awl 80 is removed and MAS 22 is engaged with opening 20 and sacrum S in threaded fixation, as shown in FIGS. 13 and 14. In one embodiment, MAS 22 is disposed such that head 40 is positioned above and/or in engagement with head 52 of alar screw 38 to prevent back out of screw 38 from plate 12 by resisting, preventing and/or blocking axial translation of alar screw 38 through opening 36.

Upon completion of a procedure, as described herein, the surgical instruments, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of rods, plates, connectors and/or bone fasteners for use with a single vertebral level or a plurality of vertebral levels.

In some embodiments, one or more of fasteners may be engaged with tissue in various orientations, such as, for example, series, parallel, offset, staggered and/or alternate vertebral levels. In some embodiments, one or more of fasteners may comprise multi-axial screws, sagittal angulation screws, pedicle screws, mono-axial screws, uni-planar screws, facet screws, fixed axis screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration.

Figure 15:
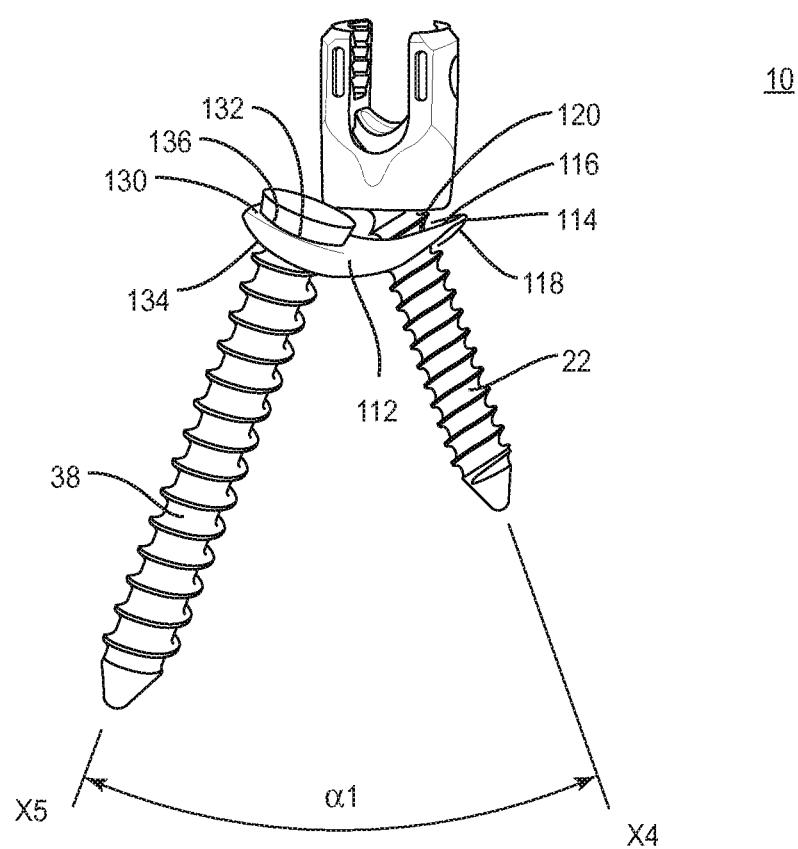
FIG. 15 is a perspective view of components of one embodiment of a system in accordance with the principles of the present disclosure.

In one embodiment, as shown in FIG. 15, system 10, similar to the systems and methods described herein, includes a medial-lateral plate 112, similar to plate 12, which can be employed with MAS 22 and alar screw 38 described herein. Plate 112 includes a substantially oblong configuration. Plate 112 includes a wall 114 having an inner surface 116 and an outer surface 118, similar to surface 18 described herein.

Wall 114 defines an opening 120 configured to receive MAS 22. Opening 120 defines an axis X4. In some embodiments, opening 120 is aligned with a surgical pathway, approach and/or trajectory, as described herein, to orient MAS 22 for implantation with tissue, such as, for example, an S1 vertebra of a sacrum S, as described herein. In some embodiments, opening 120 is aligned with a surgical pathway, approach and/or trajectory that communicates with a posterior mid-line surgical pathway, approach and/or trajectory, as described herein. In some embodiments, opening 120 includes a threaded surface configured to facilitate engagement with a threaded shaft of MAS 22, as described herein.

Plate 112 includes a wall 130 including an inner surface 132 and an outer surface 134. Surface 132 defines an opening 136. Opening 136 defines an axis X5 and is configured to receive alar screw 38. Opening 136 is configured for disposal of alar screw 38 and aligns alar screw 38 with axis X5. As such, the longitudinal axis of alar screw 38 is co-axial with axis X5. In some embodiments, opening 136 may be threaded for engagement with alar screw 38.

In some embodiments, axis X5 is disposed at a compound angle relative to axis X4. In some embodiments, axis X5 is disposed at an angle $\alpha 1$ relative to axis X4. In some embodiments, MAS 22 is aligned with axis X5 for implantation with an S1 vertebra and alar screw 38 is aligned with axis X5 for implantation with an alar region of a sacrum to attach plate 112 with a sacrum, as described herein. In some embodiments, angle $\alpha 1$ can be adjusted to facilitate a tight fit with patient anatomy.

Figure 16:
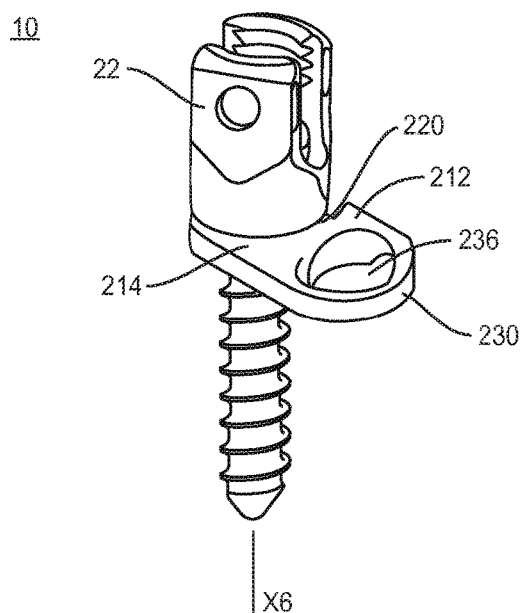
FIG. 16 is a perspective view of components of one embodiment of a system in accordance with the principles of the present disclosure.
Figure 17:
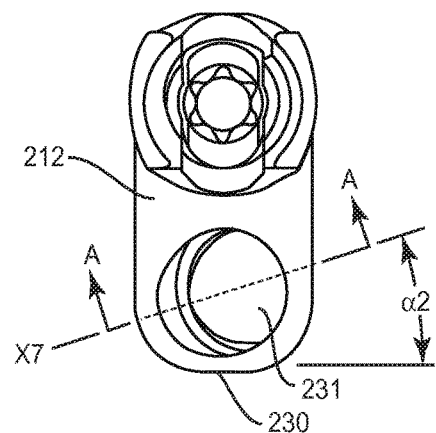
FIG. 17 is a top view of the components shown in FIG. 16.
Figure 18:
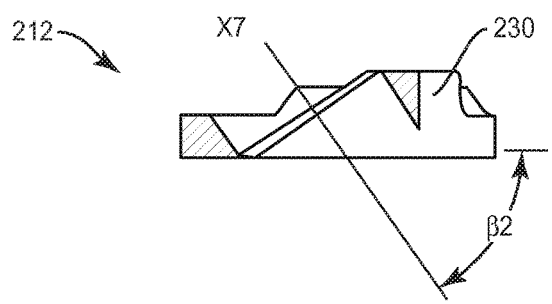
FIG. 18 is a cross section view along the line A-A shown in FIG. 17.
Figure 19:
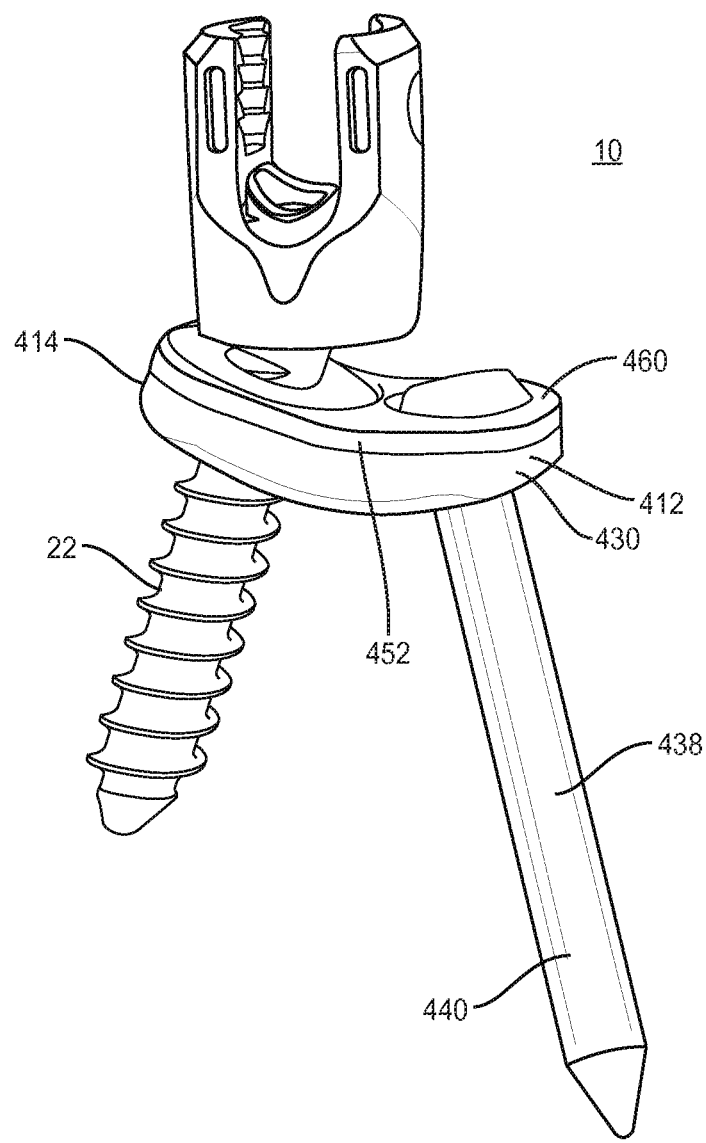
FIG. 19 is a perspective view of components of one embodiment of a system in accordance with the principles of the present disclosure.

In one embodiment, as shown in FIGS. 16-18, system 10, similar to the systems and methods described herein, includes a cephalad-caudal oriented plate 212, similar to plate 12, which can be employed with MAS 22 and an alar screw (not shown) described herein. Plate 212 includes a wall 214 that defines an opening 220 configured to receive MAS 22. Opening 220 defines an axis X6 such that opening 220 is aligned with a surgical pathway, approach and/or trajectory, as described herein, to orient MAS 22 for implantation with an S1 vertebra of a sacrum S, as described herein.

Plate 212 includes a wall 230 that defines an opening 236. Opening 236 defines an axis X7 and is configured to receive the alar screw. Opening 236 is configured for disposal of the alar screw and aligns the alar screw with axis X7. As such, the longitudinal axis of the alar screw is co-axial with axis X7. Opening 236 is disposed below opening 220 relative to a sacrum such that openings 220, 236 are disposed in a cephalad-caudal orientation with the sacrum.

In some embodiments, axis X7 is disposed at a compound angle relative to axis X6 and/or other axes of plate 212. In some embodiments, axis X7 is disposed at a compound angle relative to axis X6 and/or other axes of plate 212, which can include orientation at an angle $\alpha 2$ and at an angle $\beta 2$, as shown in FIGS. 17 and 18. As such, for example, MAS 22 is aligned with axis X6 for implantation with an S1 vertebra and the alar screw is aligned with axis X7 for implantation with an alar region of a sacrum to attach plate 212 with a sacrum, as described herein. In some embodiments, axis X7 may be oriented at a single angle relative to axis X6 and/or other axes of plate 212. In some embodiments, angle $\alpha 2$ and/or angle $\beta 2$ can include an angle in a range of approximately 0 through 90 degrees. In one embodiment, angle $\alpha 2$ is approximately 20 degrees and/or angle $\beta 2$ is approximately 45 degrees.

In one embodiment, as shown in FIGS. 19-28, system 10, similar to the systems and methods described herein, includes a multi-axial nail plate 412, similar to plate 12, which can be employed with MAS 22 described herein and an alar nail 438. Plate 412 includes a substantially oblong configuration. Plate 412 includes a wall 414 having an inner surface 416 and an outer surface 418, similar to surface 18 described herein.

Wall 414 defines an opening 420 configured to receive MAS 22. In some embodiments, opening 420 is aligned with a surgical pathway, approach and/or trajectory, as described herein, to orient MAS 22 for implantation with an S1 vertebra of a sacrum S, as described herein. In some embodiments, opening 420 includes a threaded surface.

Plate 412 includes a wall 430 including an inner surface 432 and an outer surface 434. Surface 432 defines an opening 436. Opening 436 is configured to receive alar nail 438. Alar nail 438 includes a shaft 440 and a spherical head 446. Opening 436 is configured for disposal of alar nail 438. In some embodiments, opening 420 defines an axis disposed at an angle and/or a compound angle oriented relative to an axis defined by opening 436, and/or one or more axes of plate 412, similar to that described herein. In some embodiments, opening 420 aligns MAS 22 for implantation with an S1 vertebra and opening 436 aligns alar nail 438 for implantation with an alar region of a sacrum to attach plate 412 with a sacrum, as described herein.

Figure 20:
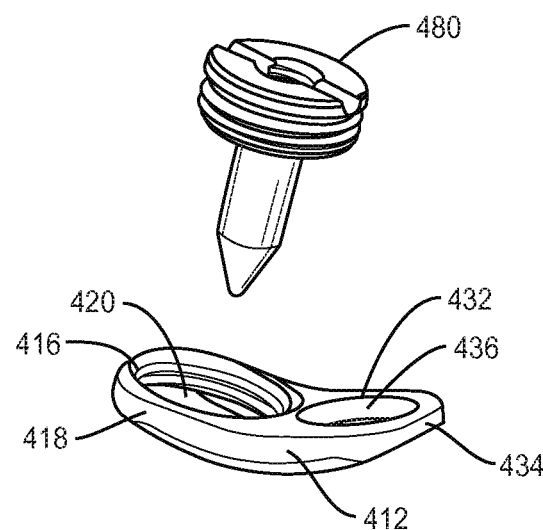
FIG. 20 is a perspective view of components of one embodiment of a system in accordance with the principles of the present disclosure.
Figure 21:
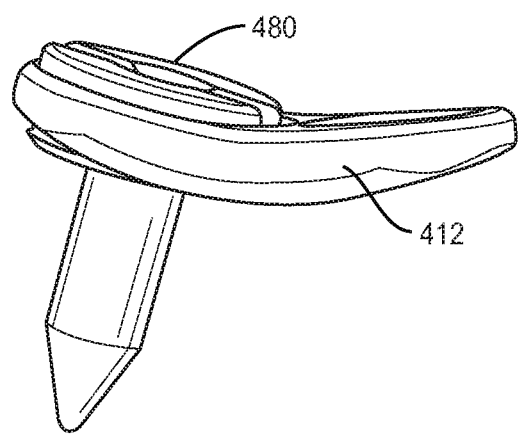
FIG. 21 is a perspective view of the components shown in FIG. 20.
Figure 22:
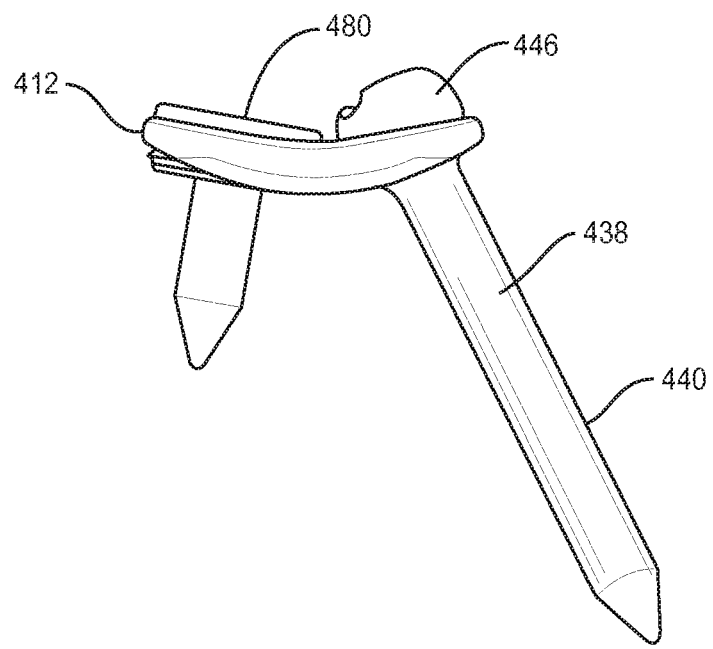
FIG. 22 is a side view of components of one embodiment of a system in accordance with the principles of the present disclosure.
Figure 23:
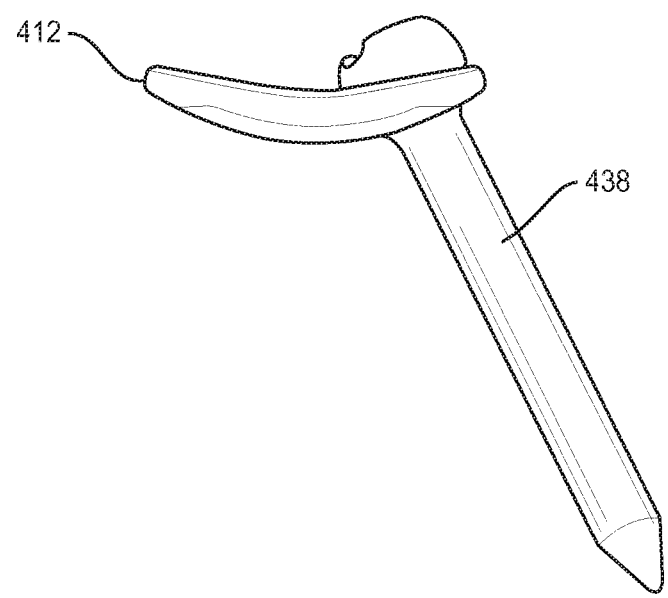
FIG. 23 is a side view of components of one embodiment of a system in accordance with the principles of the present disclosure.

In use, similar to that described herein, an awl 480, similar to awl 80 described herein, is threaded with opening 420, as shown in FIGS. 20 and 21. A tip of awl 480 is oriented to penetrate tissue of an S1 vertebra of a sacrum (not shown). Alar nail 438 is disposed with opening 436, as shown in FIG. 22, and engaged with tissue such that shaft 440 is driven into bone of the alar region of the sacrum. Awl 480 is removed from plate 412, as shown in FIG. 23.

Figure 24:
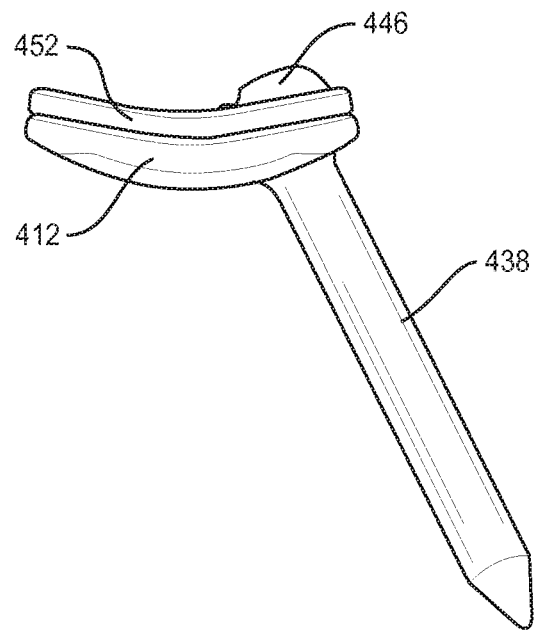
FIG. 24 is a side view of components of one embodiment of a system in accordance with the principles of the present disclosure.
Figure 25:
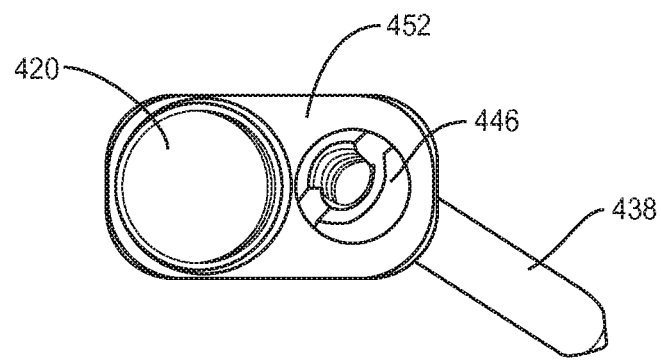
FIG. 25 is a top view of the components shown in FIG. 24.
Figure 26:
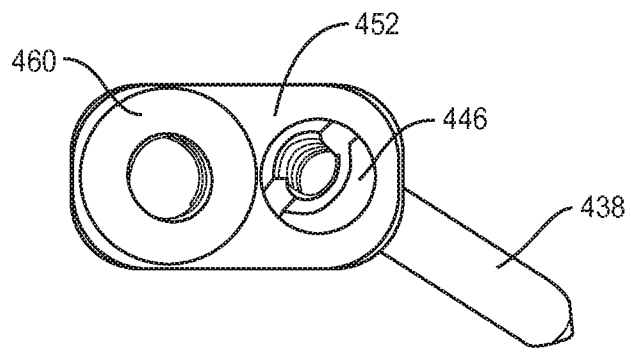
FIG. 26 is a top view of components of one embodiment of a system in accordance with the principles of the present disclosure.
Figure 27:
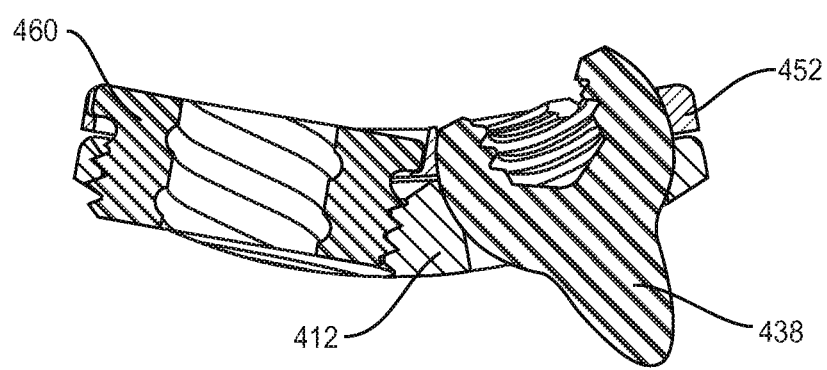
FIG. 27 is a cross section view of the components shown in FIG. 26.
Figure 28:
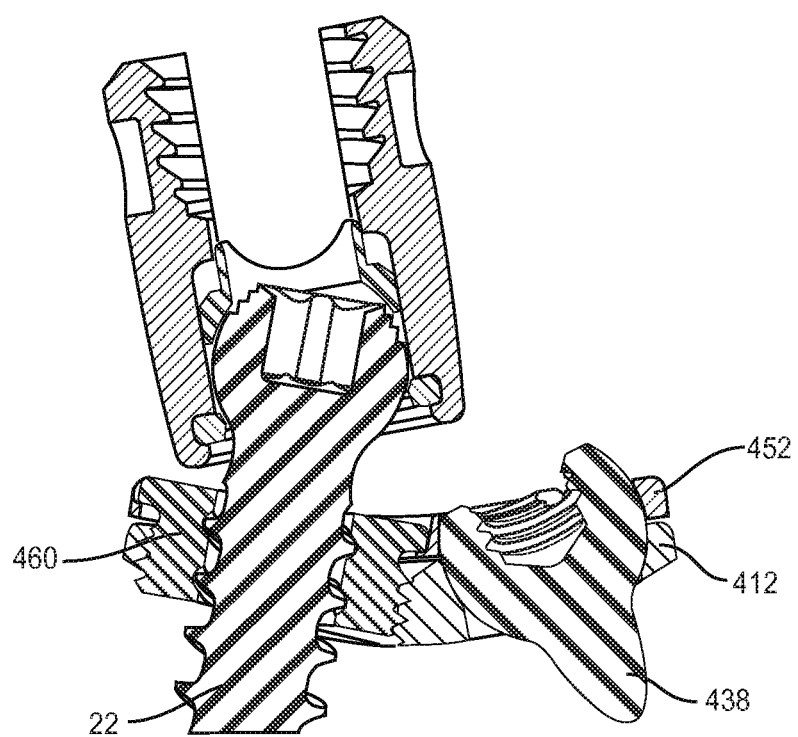
FIG. 28 is a perspective view of components of one embodiment of a system in accordance with the principles of the present disclosure.

A plate cover 452 is disposed with plate 412 to cover and/or lock head 446 and alar nail 438 with plate 412, as shown in FIGS. 24 and 25, to resist and/or prevent backout of alar nail 438 from plate 412. An insert 460, similar to insert 60 described herein, is threaded with opening 420 and cover 452, as shown in FIGS. 26 and 27. Insert 460 applies a force to cover 452 causing a locking pressure to head 446. MAS 22 is disposed with plate 412 and threaded through insert 460, as shown in FIG. 28, for fixation with an S1 vertebra of a sacrum, as described herein. The engagement of insert 460 and cover 452 resists and/or prevents backout of alar nail 438 and MAS 22 from plate 412. In some embodiments, system 10 does not include a plate cover such that MAS 22 is disposed with insert 460 and MAS 22 engages head 446 to resist and/or prevent backout of alar nail 438 from plate 412.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a multi-axial fastener comprising a threaded shaft and a head that is rotatable relative to the threaded shaft, the head comprising spaced apart arms that define a U-shaped implant cavity therebetween;
    a fastener; and
    a plate including a first cavity oriented to implant the multi-axial fastener with a sacrum and a second cavity oriented to implant the fastener with an ala of the sacrum, the multi-axial fastener being positioned within the first cavity such that the threaded shaft directly engages an inner surface of the plate that defines the first cavity, the first cavity defining a first axis and the second cavity defining a second axis that is disposed at a transverse angle relative to the first axis.

2. A spinal implant as recited in claim 1, wherein each of the cavities are configured for alignment with a pathway that communicates with a posterior mid-line surgical approach.

3. A spinal implant as recited in claim 1, wherein the first cavity is oriented to implant the multi-axial fastener with an S1 vertebra of the sacrum.

4. A spinal implant as recited in claim 1, wherein the plate comprises a first wall including the first cavity and a second wall including the second cavity, the first wall being disposed at an angle relative to the second wall.

5. A spinal implant as recited in claim 4, wherein the first wall includes an outer surface engageable with tissue of an S1 vertebra of the sacrum and the second wall includes an outer surface engageable with tissue of the ala.

6. A spinal implant as recited in claim 1, further comprising an insert disposable in at least one of the cavities.

7. A spinal implant as recited in claim 6, wherein the insert comprises one of a plurality of inserts having alternately sized openings.

8. A spinal implant as recited in claim 1, further comprising an awl configured for disposal with the first cavity to provisionally fix placement of the plate.

9. A spinal implant as recited in claim 1, wherein the plate comprises visual indicia configured to provide configuration and/or dimension of the plate.

10. A spinal implant as recited in claim 1, wherein the plate includes a first wall thickness that includes the first cavity and a second wall thickness that includes the second cavity, the second wall thickness being greater than the first wall thickness.

11. A spinal implant as recited in claim 1, wherein the plate defines a longitudinal axis, the first cavity being aligned with the longitudinal axis and the second cavity being offset from the longitudinal axis.

12. A spinal implant as recited in claim 1, wherein the plate extends along a horizontal axis between a first end that includes the first cavity and an opposite second end that includes the second cavity, the second axis being disposed at a first angle relative to the horizontal axis in a lateral direction and at a second angle relative to the horizontal axis in a cephalad-caudal direction.

13. A spinal implant as recited in claim 12, wherein the first angle is approximately 20 degrees.

14. A spinal implant as recited in claim 12, wherein the second angle is approximately 45 degrees.

15. A spinal implant as recited in claim 1, wherein the plate extends along a horizontal axis between a first end that includes the first cavity and an opposite second end that includes the second cavity, the second axis being disposed at a single angle relative to the horizontal axis.

16. A spinal implant comprising:
    a multi-axial fastener having a head and a shaft, the head comprising spaced apart arms that define a U-shaped implant cavity therebetween;
    a fastener; and
    a plate including a first cavity oriented to implant the multi-axial fastener with a sacrum and a second cavity oriented to implant the fastener with an ala of the sacrum, the head having a maximum diameter that is greater than that of the first cavity, the multi-axial fastener being positioned within the first cavity such that threads on the shaft directly engage an inner surface of the plate that defines the first cavity.

17. A spinal implant comprising:
    a plate extending along a horizontal axis between a first end that includes a first cavity and an opposite second end that includes a second cavity, the first cavity defining a first axis and the second cavity defining a second axis that is disposed at an acute angle relative to the first axis, the first axis extending perpendicular to the horizontal axis and the second axis extending at an acute angle relative to the horizontal axis;
    a first screw comprising a threaded shaft and a head connected to the shaft such that the head is rotatable relative to the shaft, the head comprising spaced apart arms that define an implant cavity therebetween, the shaft being positioned within the first cavity such that threads of the shaft directly engage an inner surface of the plate that defines the first cavity and the head is spaced apart from the plate; and
    a second screw comprising a threaded shaft and a head connected to the shaft of the second screw, the shaft of the second screw being positioned within the second opening such that the head of the second screw engages the plate.

18. A spinal implant as recited in claim 17, wherein the head of the first screw has a maximum diameter that is greater than that of the first cavity.

* * * * *

UNITED STATES PATENT AND TRADEMARK OFFICE
CERTIFICATE OF CORRECTION

PATENT NO. : 9,872,711 B2  
APPLICATION NO. : 14/520054  
DATED : January 23, 2018  
INVENTOR(S) : Hynes et al.

Page 1 of 1

It is certified that error appears in the above-identified patent and that said Letters Patent is hereby corrected as shown below:

On the Title Page

In Item (72), under "Inventors", in Column 1, Line 3, delete "Rodney R Ballard," and insert -- Rodney R. Ballard, --, therefor.

In Item (73), under "Assignee", in Column 1, Line 1, delete "Warsaw Orthopedic. Inc.," and insert -- Warsaw Orthopedic, Inc., --, therefor.

In the Specification

In Column 1, Line 3, delete "TECHNICAL HELD" and insert -- TECHNICAL FIELD --, therefor.

In Column 2, Line 17, delete "of system" and insert -- of a system --, therefor.

In Column 6, Line 64, delete "(TOP)," and insert -- (TCP), --, therefor.

Signed and Sealed this  
Fourteenth Day of August, 2018

Andrei Iancu  
*Director of the United States Patent and Trademark Office*